US00PP33228P2

(12) United States Plant Patent
Wood

(10) Patent No.: US PP33,228 P2
(45) Date of Patent: Jul. 6, 2021

(54) ***CHAMAECYPARIS* PLANT NAMED 'SMNCLMG'**

(50) Latin Name: *Chamaecyparis lawsoniana*
Varietal Denomination: SMNCLMG

(71) Applicant: Spring Meadow Nursery, Inc., Grand Haven, MI (US)

(72) Inventor: Timothy D Wood, Spring Lake, MI (US)

(73) Assignee: Spring Meadow Nursery, Grand Haven, MI (US)

( * ) Notice: Subject to any disclaimer, the term of this patent is extended or adjusted under 35 U.S.C. 154(b) by 0 days.

(21) Appl. No.: 17/039,175

(22) Filed: Sep. 30, 2020

(51) Int. Cl.
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ..... A01H 7/00
See application file for complete search history.

*Primary Examiner* — Kent L Bell
(74) *Attorney, Agent, or Firm* — Cassandra Bright

(57) ABSTRACT

A new and distinct variety of *Chamaecyparis* plant named 'SMNCLMG' is disclosed, characterized by a fresh green foliage color which is well maintained. Plants are compact and full with a teardrop shape. Plants are low maintenance. The new cultivar is a *Chamaecyparis*, suitable for ornamental garden purposes.

2 Drawing Sheets

Latin name of the genus and species: *Chamaecyparis lawsoniana.*
Variety denomination: 'SMNCLMG'.

BACKGROUND OF THE INVENTION

The new *Hydrangea* cultivar is a product of a planned breeding program conducted by the inventor, at a commercial nursery in Grand Haven, Mich. The objective of the breeding program was to produce new *Chamaecyparis* varieties with new low maintenance growth, good foliage texture and interesting foliage colors. The open-pollination resulting in this new variety was made during July of 2006. Parent varieties cannot be identified. 'SMNCLMG' was selected during 2010 at the same commercial nursery in Grand Haven, Mich.

After identifying the new variety as a potentially interesting selection, first propagation of 'SMNCLMG' occurred by softwood cuttings at a commercial nursery in Grand Haven, Mich. in 2010. The inventor continued controlled testing and propagation, assessing stability of the unique characteristics of this variety. Five generations have been reproduced and have shown that the unique features of this cultivar are stable and reproduced true to type.

SUMMARY OF THE INVENTION

The cultivar 'SMNCLMG' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SMNCLMG'. These characteristics in combination distinguish 'SMNCLMG' as a new and distinct *Chamaecyparis* cultivar:

1. Compact and very full plant habit.
2. Fresh green color is well maintained.
3. Teardrop plant shape.

COMMERCIAL COMPARISON

'SMNCLMG' can be compared to the commercial variety *Chamaecyparis lawsoniana* 'Minima Aurea', unpatented.

The varieties are similar in most horticultural characteristics, however, plants of 'SMNCLMG' differ in the following ways:

1. Plants of the new variety are narrower, having a more teardrop shape; plants of this comparator are wider and more columnar.
2. Branches of the new variety grow both upwards and outward; branches of this comparator grow mostly upwards.

BRIEF DESCRIPTION OF THE PHOTOGRAPHS

Figure 1:
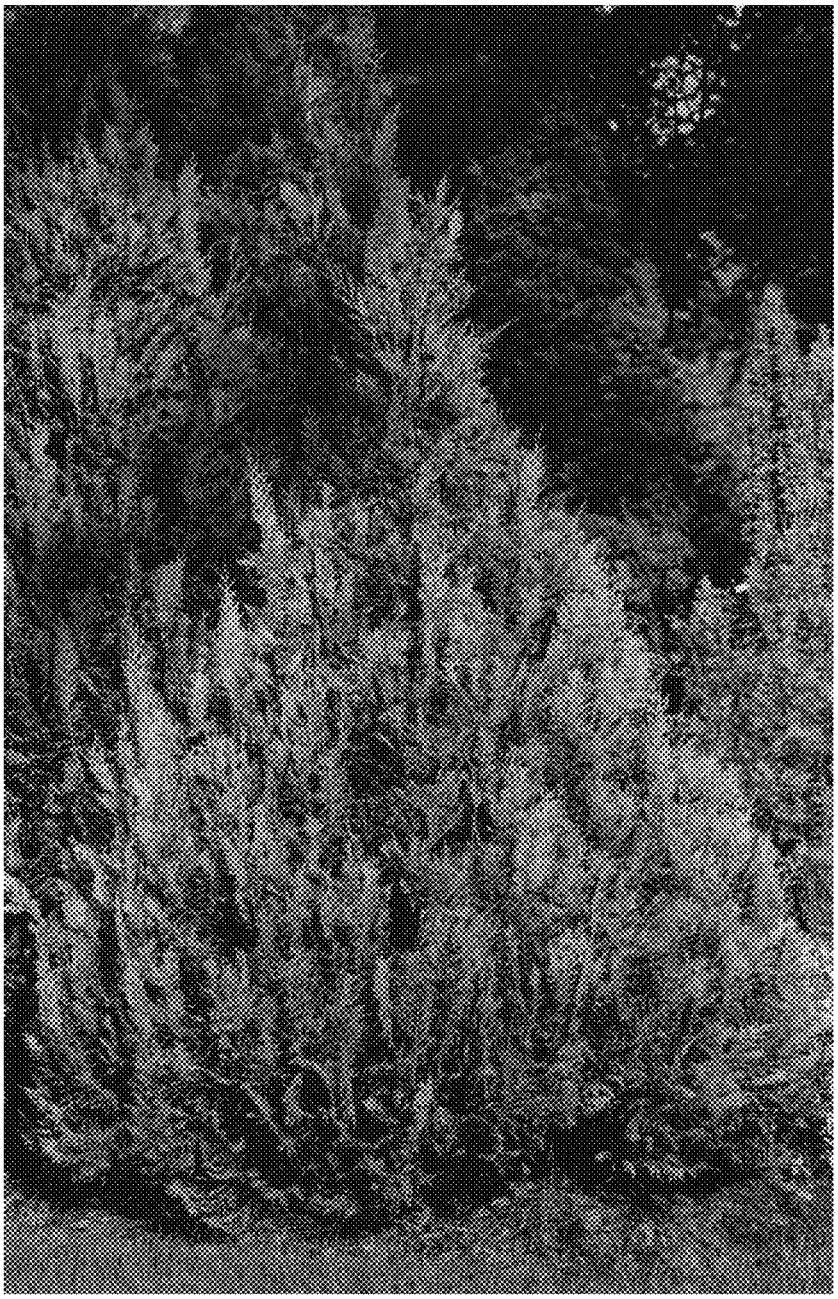

The accompanying photograph in FIG. 1 illustrates in full color typical foliage of 'SMNCLMG' grown outdoors in Grand Haven, Mich. at about 8 years of age.

Figure 2:
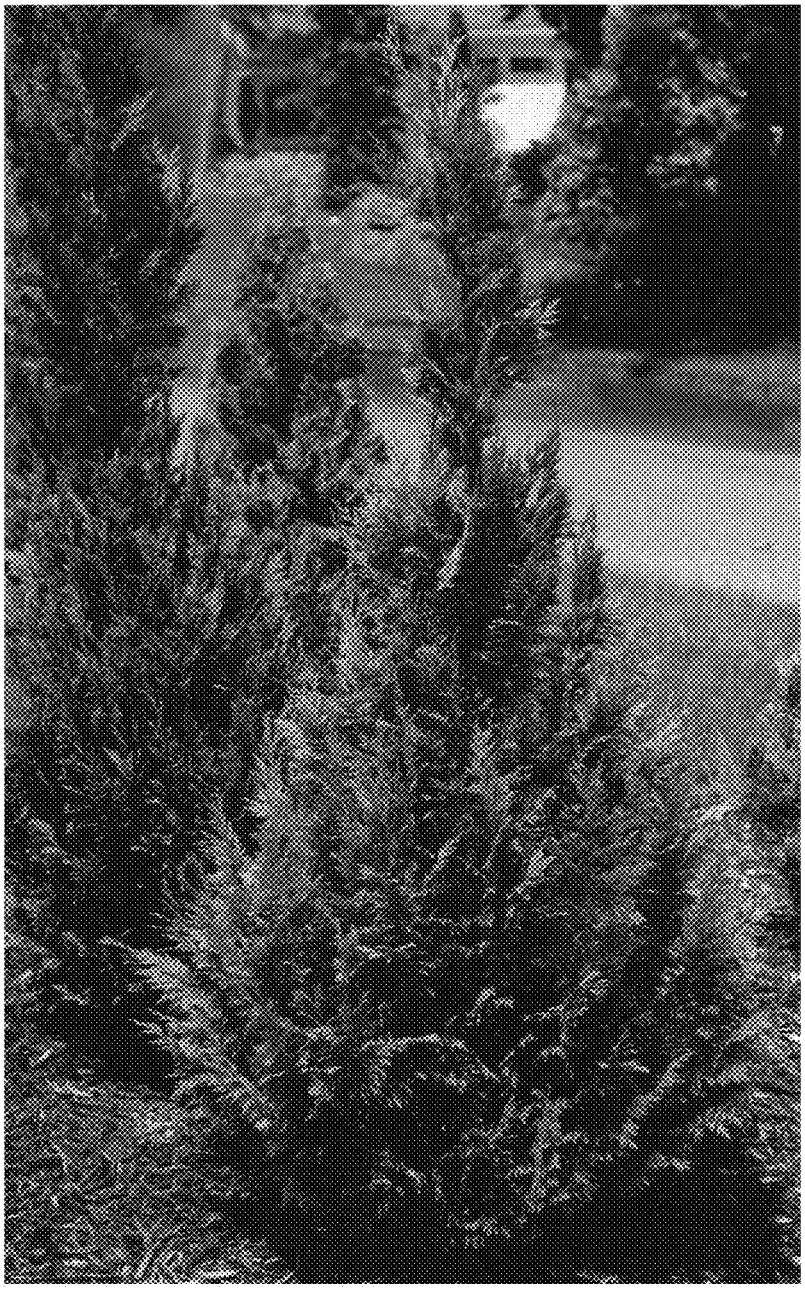

FIG. 2 illustrates a plant of the new variety at approximately 2 years old, also grown outdoors in Grand Haven, Mich.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMNCLMG' plants grown in a poly greenhouse during Summer, in Grand Haven, Mich. USA. The growing temperature ranged from 18° C. to 27° C. during the day and from 5° C. to 10° C. during the night. General light conditions are natural sunlight. Measurements and numerical values represent averages of typical plant types. Measurements were taken during August of 2020.

Botanical classification: *Chamaecyparis lawsoniana* 'SMNCLMG'.

PROPAGATION

Typical method: Softwood cuttings.
Time to initiate rooting: 120 days at approximately 10° C.
Time to produce a rooted young plant: 180 days at approximately 10° C. to 13° C.

PLANT

Age of plant described: 2 years.
Container size of plant described: 3 gallon.
Growth habit: Upright, teardrop-shaped evergreen tree.
Height: 75 cm.
Plant spread: 58 cm.
Typical growth rate: Moderate.
Pinching required: Preferred to encourage branching, not required.
Branching characteristics:
*Angle*.—About 0° to 45° from main leader.
*Quantity of lateral branches*.—About 20.
Length of lateral branches: Average 42 cm.
Diameter of lateral branches: Average 8 mm.
Lateral branch shape: Round with overlapping scales.
Stem strength: Very strong and flexible.
Stem color:
*Young*.—Greyed-Orange 176B with some Green 143C.
*Older*.—Greyed-Brown 199C.
Internode length: 1 cm.
Root description: Fine and fleshy roots present. Moderately well branched. Colored light brown, not accurately measured with an R.H.S. chart.

FOLIAGE

General description: Overlapping scales.
Leaf:
*Arrangement*.—Alternate overlapping scales.
*Shape of blade*.—Scale-like.
*Average length*.—3 mm.
*Average width*.—1 mm.
*Apex*.—Apiculate.
*Base*.—Cuneate.
*Margin*.—Entire
*Texture of top surface*.—Smooth.
*Texture of bottom surface*.—Smooth.
*Foliage color*.—Young, upper side: Near Green 143C with tips Yellow-Green 151A. Young, under side: Near Green 143C with tips Yellow-Green 151A. Mature, upper side: Near Green 139C. Mature, under side: Near Green 139C.
*Venation*.—Indistinguishable from leaf blade.
*Fragrance*.—Not observed.

FLOWER

Flowering not observed.

OTHER CHARACTERISTICS

Disease and pest resistance: Neither resistance nor susceptibility observed.
Drought tolerance: No tolerance for drought.
Temperature tolerance: −29 to 36° C.

What is claimed is:

1. A new and distinct cultivar of *Chamaecyparis* plant named 'SMNCLMG' as herein illustrated and described.

* * * * *